(12) United States Patent
Tseng et al.

(10) Patent No.: US 8,729,260 B2
(45) Date of Patent: *May 20, 2014

(54) PROCESS FOR THE PREPARATION OF CARBAPENEM USING CABAPENEM INTERMEDIATES AND RECOVERY OF CABAPENEM

(75) Inventors: Wei-Hong Tseng, Miaoli County (TW);
Wen-Hsin Chang, Miaoli County (TW);
Chia-Mao Chang, Miaoli County (TW);
Chia-Wei Yeh, Miaoli County (TW);
Yuan-Liang Kuo, Miaoli County (TW)

(73) Assignee: Savior Lifetec Corporation, Miaoli County (TW)

( * ) Notice: Subject to any disclaimer, the term of this patent is extended or adjusted under 35 U.S.C. 154(b) by 1 day.

This patent is subject to a terminal disclaimer.

(21) Appl. No.: 13/100,635

(22) Filed: May 4, 2011

(65) Prior Publication Data

US 2011/0288290 A1    Nov. 24, 2011

Related U.S. Application Data

(63) Continuation-in-part of application No. 12/783,166, filed on May 19, 2010, now abandoned.

(51) Int. Cl.
*C07D 487/04* (2006.01)
*C07D 477/20* (2006.01)

(52) U.S. Cl.
CPC .................... *C07D 477/20* (2013.01)
USPC ...................................... 540/350

(58) Field of Classification Search
CPC .................................... C07D 477/20
USPC ...................................... 540/350
See application file for complete search history.

(56) References Cited

U.S. PATENT DOCUMENTS

| 5,478,820 | A | 12/1995 | Betts et al. | |
| 5,487,820 | A | 1/1996 | Huber et al. | |
| 5,856,321 | A * | 1/1999 | Betts et al. | 514/210.13 |
| 6,180,783 | B1 | 1/2001 | Williams et al. | |
| 6,504,027 | B1 | 1/2003 | Williams et al. | |
| 2009/0312539 | A1* | 12/2009 | Rao et al. | 540/350 |
| 2012/0015932 | A1* | 1/2012 | Hobbs et al. | 514/210.18 |
| 2012/0035357 | A1* | 2/2012 | Kanagaraj et al. | 540/350 |
| 2012/0065392 | A1* | 3/2012 | Song et al. | 540/350 |
| 2012/0095209 | A1* | 4/2012 | Shi et al. | 540/350 |

FOREIGN PATENT DOCUMENTS

WO    WO 2011141847 A1 * 11/2011

OTHER PUBLICATIONS

J. Michael Williams et al., Practical Synthesis of the New Carbapenem Antibiotic Ertapenem Sodium, The Journal of Organic Chemistry, 2005, pp. 7479-7487, vol. 70, No. 19.

Anant Vailaya et al., Exploiting pH mismatch in preparative high-performance liquid chromatographic recovery of ertapenem from mother liquor streams, Journal of Chromatography A, 2005, pp. 80-91, vol. 1079.

Stephen M. Berge et al., Pharmaceutical Salts, Journal of Pharmaceutical Sciences, Jan. 1977, pp. 1-19, vol. 66, No. 1.

* cited by examiner

*Primary Examiner* — Andrew D Kosar
*Assistant Examiner* — John S Kenyon
(74) *Attorney, Agent, or Firm* — WPAT, P.C.; Anthony King; Kay Yang

(57) ABSTRACT

The present invention relates to an efficient process of synthesizing some known Ertapenem compounds and to provide new intermediate compounds of Meropenem and Doripenem. The process and the intermediate can substantially increase the effective yield and reduce the impurity generation. The present invention further provides a novel and effective process for recovering and purifying ertapenem compounds by utilizing a low cost, materials with chemical stability as a carrier for isolating ertapenem compounds from extracts.

14 Claims, No Drawings

PROCESS FOR THE PREPARATION OF CARBAPENEM USING CABAPENEM INTERMEDIATES AND RECOVERY OF CABAPENEM

CROSS REFERENCE

This is a continuation-in-part of U.S. application Ser. No. 12/783,166, filed on May 19, 2010, which is incorporated herewith by reference.

BACKGROUND OF THE INVENTION

1. Field of the Invention

The present invention relates to a novel processes for the preparation of carbapenem intermediates that are useful to produce Ertapenem, Meropenem and Doripenem and further provides an effective process for recovering and purifying ertapenem compounds.

2. The Prior Arts

The carebapenem are among the most broadly effective antibiotics making them useful in the treatment of a wide range of bacterial infections including against both Gram positive and negative, aerobic and anaerobic bacteria. Since carbapenems were first isolated from fermentation media in 1974, several problems with the development of antibiotic resistance in bacteria and novel untreatable bacteria have been appeared. The continuing emergence of bacteria exhibiting resistance to existing therapeutic agents has made development of new carbapenem an important part of our strategy in addressing this problem.

Ertapenem of carbapenem antibiotics is commercially available as Invanz® from Merck, and has chemical name [4R,5S,6S]-3-[[(3S,5S)-5-[[(3-carboxyphenyl)amino]carbonyl]-3-pyrrolidinyl]-thio]-6-[(1R)-1-hydroxyethyl]-4-methyl-7-oxo-1-azabicyclo[3.2.0]hept-2-ene-2-carboxylic-acid which can be used as an intravenous infusion or intramuscular injection. 1β-methylcarbapenem antibiotic is Ertapenem of formula (II) in the present invention, and used as antibiotic agent in the treatment of moderate to severe complicated foot infection due to indicated pathogens in diabetic patients without osteomyelitis, 1β-methylcarbapenem antibiotic is also useful in the treatment of pneumonia, urinary tract infections, intra-abdominal, gynecological, skin, and soft tissue infections, meningitis, septicemia and febrile Neutrogena.

In view of the importance of 1β-methylcarbapenem antibiotic, several synthetic procedures to prepare the compound have been reported. U.S. Pat. No. 5,478,820 and U.S. Pat. No. 5,856,321 claim various processes for preparing Ertapenem and its sodium salt. Example 12 of U.S. Pat. No. 5,487,820 discloses a process in which the Ertapenem was isolated by using column purification as well as freeze-drying technique. Example 1 of U.S. Pat. No. 6,180,783 also provides an improved process for carbapenem synthesis by using hydrophobic resin purification and then nanofiltration to obtain the product in the stabilized form. Therefore, this is an expensive, labor intensive technique, and the long-time process may cause instability of the product.

U.S. Pat. No. 6,504,027 provides a process for preparing Ertapenem in crystalline form and the document also reported about development of a procedure for the production of the ertapenem (J. Org. Chem. 2005, 70, 7479-7487). However, the process for deprotecting the mono-protected Ertapenem is more complicated and more unstable intermediates therein and the reaction conditions is more stringent and higher material costs. In addition, there general problems with preparation of Ertapenem compounds such as occurrence of undesired by-products, complexity of synthesis, low yields, and subsequently high cost.

In the preparation of Ertapenem, consideration of above characteristics, the loss of the ertapenem in the reaction solution was about 15 to 20%. Therefore, it is necessary to develop a method for recovering and purifying of ertapenem (Ertapenem) form the reaction solution with economic and efficient steps. J. Chromatogr A. 1079, 80-91 (2005) refers to several operating procedures, such as high-pressure column chromatography (HPLC), −70° C. ultra-low temperature preservation and long-time distillation. Since these prior arts involve number of operations which are expensive, labor intensive techniques and subsequently high cost, it is not easy to carry out a great deal of recovery after using the above operating procedures.

In addition, the recovery and the purification of Ertapenem reaction solution is difficult since several reasons, such as the concentration is too low to crystallize (about 2~8 mg/ml), high levels of impurities (about 50~60%), the complex composition of the reaction solution, and the product is damaged with time.

SUMMARY OF THE INVENTION

The aim of the present invention is to provide novel efficient processes of synthesizing some known Ertapenem compounds and to provide new intermediate compounds. The above process and the intermediate can substantially increase the effective yield and reduce the impurity generation. The present invention further provides a novel and effective process for recovering and purifying ertapenem compounds by utilizing a low cost, materials with chemical stability as a carrier for isolating ertapenem compounds from extracts, and the above process is significant for the industrial production.

Accordingly, the present invention provides a novel process for preparing compounds of formula II:

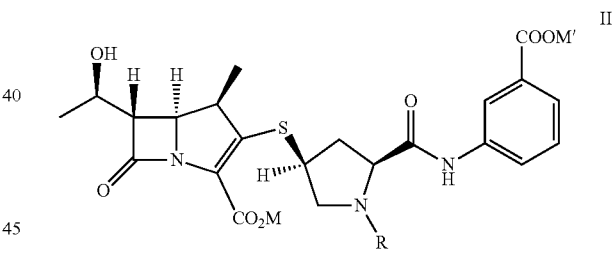

or a pharmaceutically acceptable salt thereof, wherein R is hydrogen or a protecting group which is carbobenzyloxy or p-nitrobenzyl carbamoyl (PNZ), and M and M' is hydrogen, sodium ion, or potassium ion respectively, comprising: providing a compound of formula Ia:

Ia

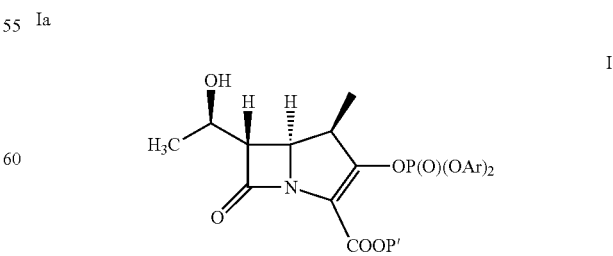

Ar = 2,4-dichlorophenyl wherein Ar is 2,4-dichlorophenyl, P is phosphor, and P' is selected from the group consisting of alkyl, 2,2,2,-trichloroethyl, 2-bromoethyl, benzhydryl, trityl, aryl, trimethylsilyl, triethylsilyl, 4-methoxybenzyl, t-butyl, p-nitrobenzyl, hydrogen, and the like.

Then the processes are performed by converting the compound of formula Ia into the compound of formula II, wherein Ar is 2,4-dichlorophenyl, P is phosphor, and P' is selected from the group consisting of alkyl, 2,2,2,-trichloroethyl, 2-bromoethyl, benzhydryl, trityl, aryl, trimethylsilyl, triethylsilyl, 4-methoxybenzyl, t-butyl, p-nitrobenzyl, and the like; and wherein the converting comprises the step of condensing the compound of formula Ia with a compound of formula V to form a compound of formula VI:

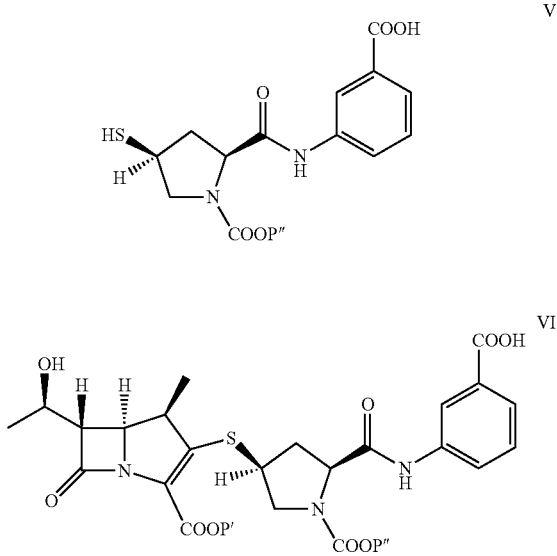

wherein P" is selected from the group consisting of alkyl, 2,2,2,-trichloroethyl, 2-bromoethyl, benzhydryl, trityl, aryl, trimethylsilyl, triethylsilyl, 4-methoxybenzyl, t-butyl, p-nitrobenzyl, hydrogen, and the like.

The present invention relates to formula Ia is a novel carbapenem intermediate, and in one embodiment, the compound of formula II, which is in amorphous form, is 1β-methylcarbapenem antibiotic.

The objective of the present invention is to provide a simple, commercially viable, and industrially scalable process for the preparation of 1β-methylcarbapenem antibiotic, which shortens the reaction time, gets a higher yield and better purity and other advantages, avoids complex post-processing problems caused by excessive impurity increase, and reduces manufacturing costs. And the present invention also provides a commercially viable and industrially scalable process for the preparation of Meropenem and Doripenem.

The present invention further provides a process for recovering and purifying the compound of formula II from the concentrated extract undergo crystallization; comprising: removing organic solvents; vacuum distilling for removing residual organic solvents to form a solution containing the compound of formula II; passing the solution through an absorbent resin (e.g. Ion Exchange Resin HP-20 or SX-10) for removing impurities by eluting with a mixture of a organic solvent-in-water to obtain an eluent; and concentrating the eluent, and then purifying and isolating to obtain the compound of formula II which is detected its purity by using high performance liquid chromatography (HPLC) assay.

The above process for recovering and purifying the compound of formula II can be effectively recovered a great deal in a simple environment and obtained more than 70% purity, the yield of 70% or more, and can be obtained the compound of formula II more than 95% purity and the total yield of 50% after post-processing. On the industrial production, the process is simple, and less time-consuming, and the chemical property of the carrier for isolation is stable, good repeatability, long life, and easy to re-use.

The details of one or more embodiments of the invention are set forth in the description below. Other features, objects, and advantages of the invention will be apparent from the description and from the claims.

DETAILED DESCRIPTION OF THE PREFERRED EMBODIMENT

According to the following reaction in Scheme 1, the 1β-methylcarbapenem antibiotic of formula II can be conveniently and economically prepared by reacting between formula I and formula V to obtain the compound of formula VI. The 1β-methylcarbapenem antibiotic of formula II is resulted from deprotecting the protecting group of formula VI in presence of a metal catalyst and a base.

The compound of formula I is condensed with compound of formula V in the presence of a base and in the presence of a solvent to obtain the compound of formula VI, wherein the base is diisopropylethylamine (DIPEA), diisopropylamine (DIPA), dicyclohexylamine (DCHA), 2,2,6,6-tetra-methylpiperidine (TMP), 1,1,3,3-tetra-methylguanidine (TMG), 1,8-diazabicyclo[4.3.0.]undec-7-ene (DBU), 1,5-diazabicyclo[4.3.0]non-5-ene (DBN), N-methylpyrrolidine, N,N-dimethyl-aminopyridine, N,N-diethyl-aminopyridine, potassium hydroxide, sodium carbonate, sodium hydrogen carbonate, or disodium hydrogen phosphate; and the preferred base is diisopropylethyl amine (DIPEA).

The solvent is selected from the group consisting of diethyl ether, tetrahydrofuran, toluene, xylene, dichloromethane, 1,2-dichloroethane, NN-dimethylformamide, dimethylacetamide, N-methylpyrrolidinone, N-ethyl-pyrrolidinone, N-methylpiperidinone, acetonitrile, propionitrile, and mixtures thereof, and the preferred solvent is acetonitrile.

The compound of formula VI is deprotected its protecting group in the presence of a metal catalyst and a base to obtain 1β-methylcarbapenem antibiotic of formula II. In one embodiment of the present invention, 1β-methylcarbapenem antibiotic of formula II is in amorphous form.

Scheme 1

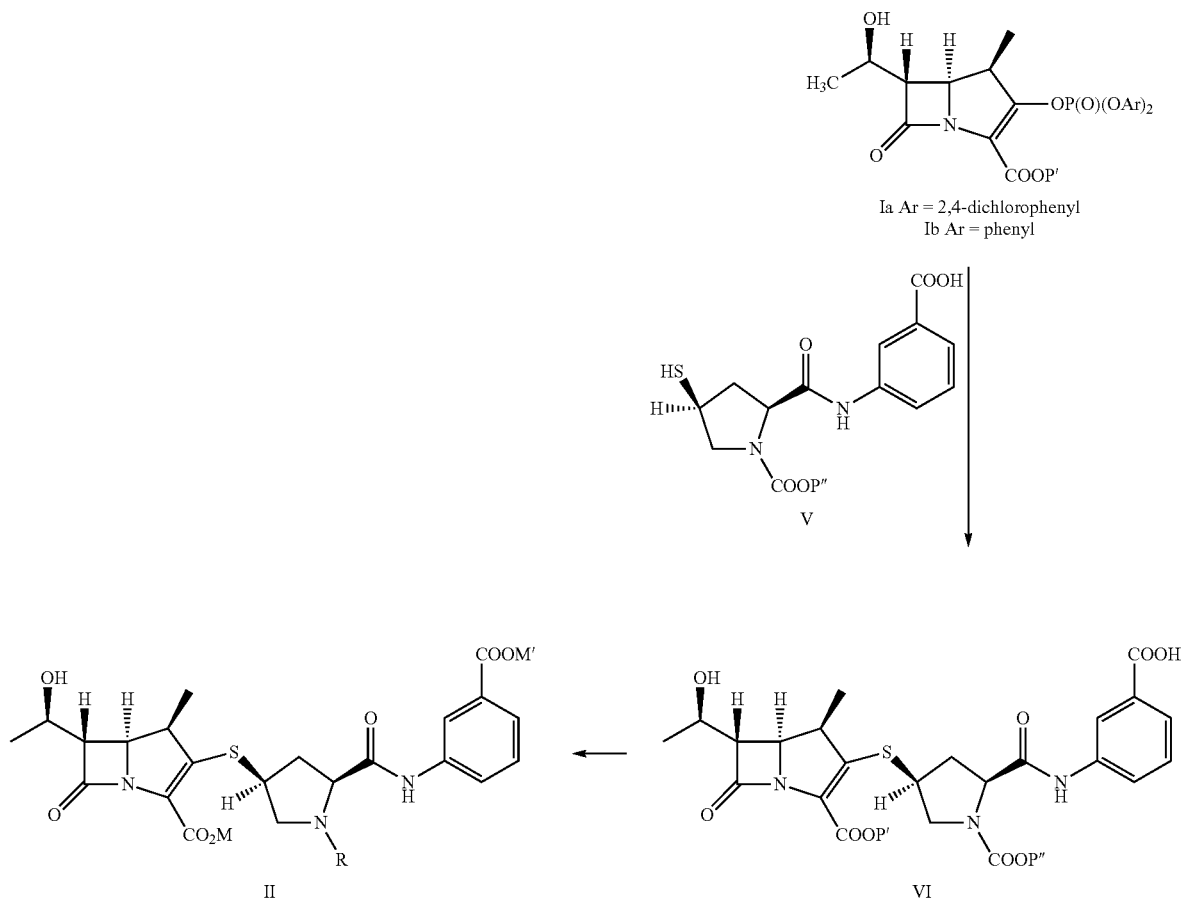

Ia Ar = 2,4-dichlorophenyl
Ib Ar = phenyl wherein Ar is 2,4-dichlorophenyl or phenyl, P is phosphor, and P' and P''' are each independently selected from the group consisting of alkyl, 2,2,2,-trichloroethyl, 2-bromoethyl, benzhydryl, trityl, aryl, trimethylsilyl, triethylsilyl, 4-methoxybenzyl, t-butyl, p-nitrobenzyl, hydrogen, and the like; or P' and P''' are preferably p-nitrobenzyl; and wherein R is hydrogen or a protecting group such as carbobenzyloxy or p-nitrobenzyl carbamoyl (PNZ), which removed by hydrogenolysis and M and M' are hydrogen, sodium ion, or potassium ion respectively.

The metal catalyst is palladium on carbon (Pd/C), platinum or platinum oxide, or the mixture thereof, and the preferred metal catalyst is palladium on carbon (Pd/C). The base is bicarbonate or hydroxide which was obtained by mixing carbon dioxide, such as sodium hydroxide, sodium bicarbonate, sodium carbonate, and the base is used for adjusting the reaction solution with pH of about 6 to 9. Since the compound of formula II is less stable at a high temperature, the need to control the reaction temperature below 20° C. to avoid producing dimmers and ring-open impurities.

The deprotection of protecting groups of the compound of formula VI can be carried out by hydrogenolysis in the presence of a metal catalyst and the reaction temperature below 20° C. Conduct hydrogen gas into the reactor and adjust the pressure more than 40 psi. After completion of the reaction, the pH value is adjusted to facilitate the filtration of solid metal catalyst, and the filtrate was added an activated carbon through thin-film distillation, extraction or other distillation methods at low temperature to remove reacted organic solvents, and then the activated carbon is removed by filtering to clarify the filtrate, then extracted using an organic solvent to remove impurities to obtain a solution containing the compound of formula II. Thus, the process is a simple and cost-effective manner with high yield, which can obtain better purity of 1β-methyl carbapenem antibiotics.

In another embodiment of the present invention, the deprotection of protecting groups using hydrogenolysis can be carried out using a mixture of solvents either in single phase or in biphasic medium. The mixture is selected from the group consisting of tetrahydrofuran (THF), acetonitrile, propionitrile, dioxane, ethylacetate, n-butanol, isopropyl alcohol, methanol, dichloromethane, NN-dimethylformamide (DMF), N-ethylpyrrolidinone, water, and mixtures thereof. The preferred mixture is a mixture of acetonitrile and water.

The volumn of aqueous layer is condensed by the extraction of n-butanol or isoamyl alcohol (IAA) to obtain high concentration of formula II in aqueous layer. Finally, a solvent is charged to the aqueous layer at a temperature in the range of −20° C. to 10° C., wherein the solvent is selected from the group consisting of methanol, ethanol, 1-propanol, isopropyl alcohol tetrahydrofuran, and mixtures thereof; and 1β-methylcarbapenem antibiotic of formula II in amorphous form is crystallized and isolated.

The process of the present invention is to synthesize some known Ertapenem compounds such as 1β-methylcarbapenem antibiotic, Meropenem, Doripenem, Ertapenem. It is preferable to use equipment that is capable of multi-stage extraction such as centrifugal extractor for optimal performance. Most preferable is the use of a multi-stage centrifugal extractor. The preferred equipment is dependent on scale; CINC (Costner Industries Nevada Corporation) liquid-liquid centrifugal separators are preferred for laboratory scale operation; whereas, a Podbielniak® centrifugal extractor is preferred for large scale operation.

The present further provides a process for recovering and purifying the compound of formula II from the concentrated extract undergo crystallization; comprising: removing organic solvents; vacuum distilling at a temperature in the range of 0° C. to 10° C. for removing residual organic solvents to form a solution containing the compound of formula II.

The above solution is passed through an absorbent resin (e.g. Ion Exchange Resin HP-20 or SX-10) at a temperature in the range of 0° C. to 5° C. for removing impurities by eluting with a mixture of a organic solvent-in-water to obtain an eluent; and concentrating the eluent, and then purifying and isolating to obtain the compound of formula II which is detected its purity by using high performance liquid chromatography (HPLC) assay.

The invention relates to a process for the preparation of the novel compound of formula Ia as defined above.

For the purpose, a compound of formula III, wherein P' is selected from the group consisting of alkyl, 2,2,2,-trichloroethyl, 2-bromoethyl, benzhydryl, trityl, aryl, trimethylsilyl, triethylsilyl, 4-methoxybenzyl, t-butyl, p-nitrobenzyl, hydrogen, and the like, is cyclized with a rhodium catalyst in dichloromethane (DCM) at a temperature in the range of 30° C. to 60° C. to obtain a compound of formula IV. As used herein, the term "rhodium catalyst" refers to dimeric rhodium salts selected from the group consisting of rhodium octanoate $Rh_2(Oct)_4$, rhodium acetate $Rh_2(Ac)_4$, rhodium octanate $Rh_2(HAc)_4$ and rhodium trifluoroacetate $Rh_2(O_2CCF_3)_4$.

The compound of formula IV is reacted with bis(2,4-dichlorophenyl)-chlorophosphate (DDCP) or bisphenyl chlorophosphate (DPCP) in the presence of a base to obtain the compound of formula I shown in Scheme 2.

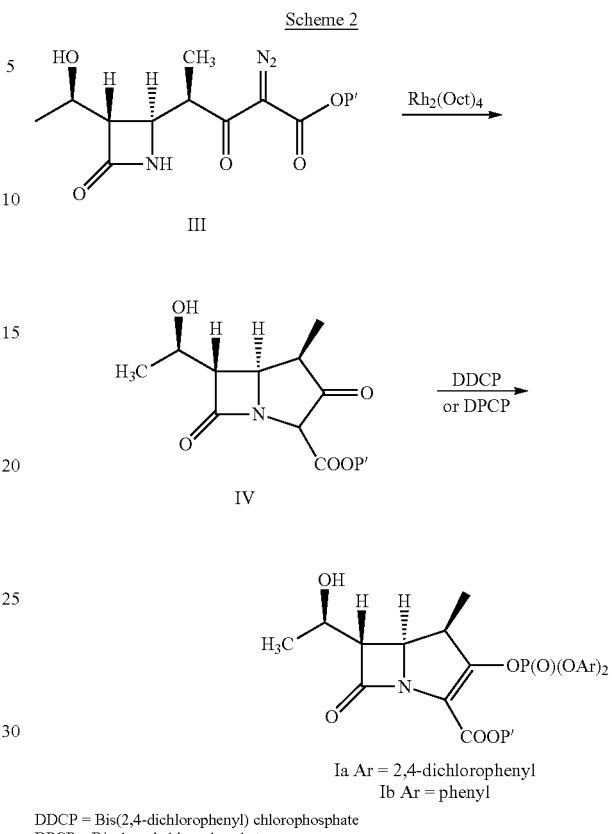

Scheme 2

Ia Ar = 2,4-dichlorophenyl
Ib Ar = phenyl

DDCP = Bis(2,4-dichlorophenyl) chlorophosphate
DPCP = Bisphenyl chlorophosphate

A process of cyclizing a compound of formula III is performed using a organic solvent selected from the group consisting of dichloromethane, methyl acetate, ethyl acetate, toluene, tetrahydrofuran, acetonitrile, and mixtures thereof. And preparation of formula I by reacting the compound of formula IV with bis(2,4-dichlorophenyl)-chlorophosphate (DDCP) or bisphenyl chlorophosphate (DPCP) in the presence of an organic base such as diisopropylethylamine (DIPEA), diisopropylamine (DIPA), dicyclohexylamine (DCHA), 2,2,6,6-tetra-methylpiperidine (TMP), 1,1,3,3-tetra-methylguanidine (TMG), 1,8-diazabicyclo[4.3.0.]undec-7-ene(DBU)1,5-diazabicyclo[4.3.0]non-5-ene(DBN), N-methylpyrrolidine, N,N-dimethyl-aminopyridine, N,N-diethylamino pyridine potassium hydroxide, sodium carbonate, sodium hydrogen carbonate, or disodium hydrogen phosphate. The preferred base is diisopropylethylamine (DIPEA). To avoid impurity formation, the condensation reaction can be optionally conducted in a base like N,N-dimethyl aminopyridine, N,N-diethylamino pyridine.

Compounds of formula I as carbapenem intermediates can be used to prepare many of carbapenem antibiotics such as 1β-methylcarbapenem antibiotic, Meropenem, Doripenem, Ertapenem, etc. as shown in Scheme 3. The compound of formula Ib is a commercial product. The present invention provides a novel compound of formula Ia. The compound of formula Ia is reacted with sulfur side chain to obtain the protected carbapenem product with higher yield and purity than the compound of formula Ib.

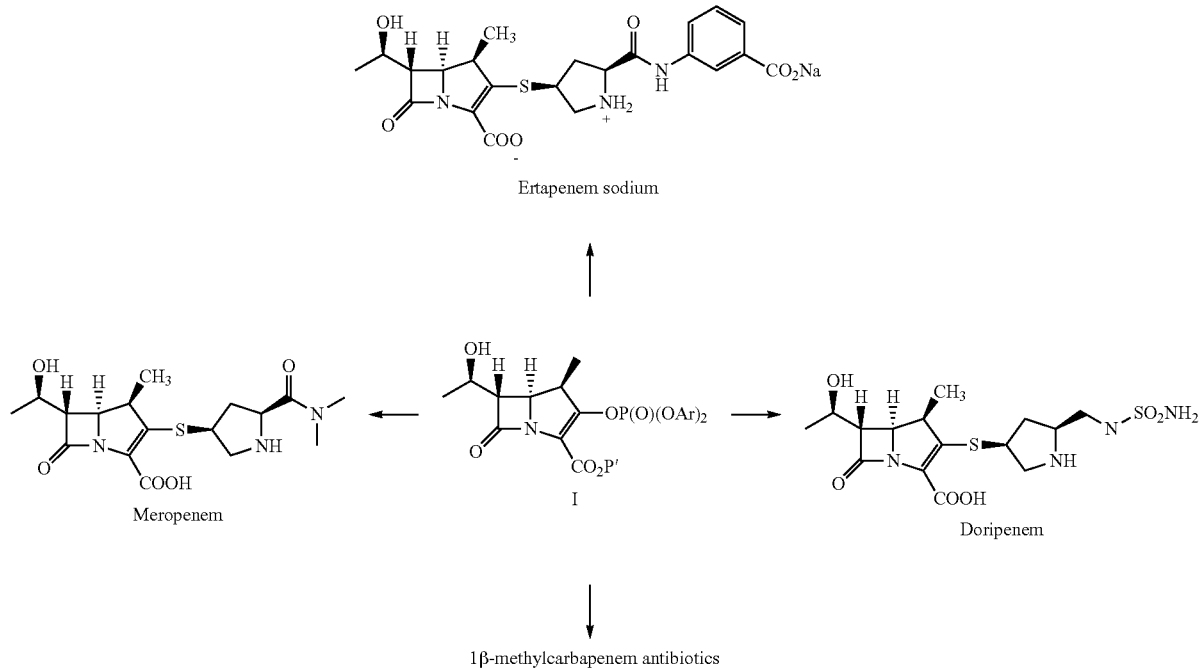

The formula I can be readily converted to Meropenem and Doripenem by one of several methods shown in Scheme 4. Meropenem prepared by reacting between formula I and formula VII to obtain the compound of formula VIII. Meropenem is resulted from deprotecting the protecting group of formula VIII in presence of a metal catalyst and a base. In addition, Doripenem prepared by reacting between formula I and formula IX to obtain the compound of formula X, wherein Ar is 2,4-dichlorophenyl. Doripenem is resulted from deprotecting the protecting group of formula X in presence of a metal catalyst and a base,

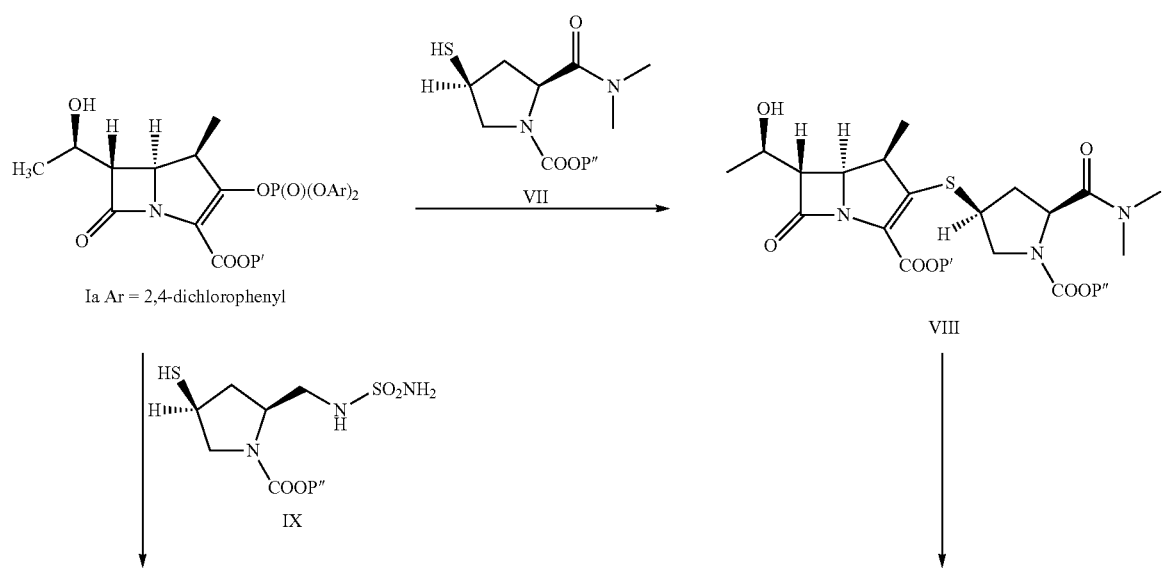

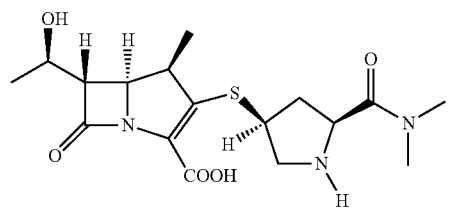

Meropenem

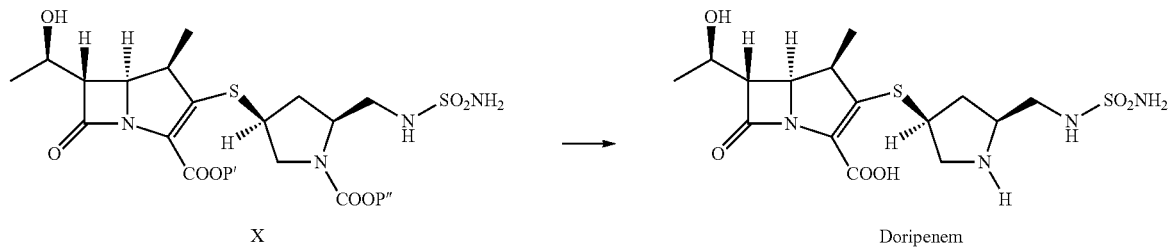

X                                Doripenem wherein Ar is 2,4-dichlorophenyl, P is phosphor, and P" and P'" are each independently selected from the group consisting of alkyl, 2,2,2,-trichloroethyl, 2-bromoethyl, benzhydryl, trityl, aryl, trimethylsilyl, triethylsilyl, 4-methoxybenzyl, t-butyl, p-nitrobenzyl, hydrogen, and the like; or P' and P'" are preferably p-nitrobenzyl.

A further embodiment of the present invention concerns the use of the compound of formula I and processes of any of the preceeding claims for the preparation of a compound of formula I.

In addition, the present invention relates to the use of compound of formula I for the preparation of 1β-methylcarbapenem antibiotic, Meropenem and Doripenem which are commercially available.

Of the compounds, the invention relates especially to those of formulae I to X as such, especially those in which the substituents correspond to the radicals indicated in the respective Examples.

Numerous salt-forming ions are recited in Berge, S. M., et al. J. Pharm. Sci. 66(1): 1 16 (1977), the teachings of which are incorporated herein by reference. The charge balancing group $X^+$ maintains overall charge neutrality. Preferably $X^+$ represents a pharmaceutically acceptable salt-forming cation. Preferred salt-forming cations are selected from the group consisting of: sodium, potassium, calcium and magnesium. More preferably the salt-forming cation is a member selected from the group consisting of: $Na^+$, $Ca^{+2}$ and $K^+$.

The present invention further provides a process for recovering and purifying the compound of formula II from the concentrated extract undergo crystallization, comprising: i) removing the organic solvent with a extracting solvent, and then distilling to form a second solution containing the compound of formula II, wherein the extracting solvent is dichloromethane, ethyl acetate, toluene, or xylene; ii) passing the second solution through an absorbent resin for removing impurities and desorbing the compound of formula II form the absorbent resin by eluting with a mixture of about 0% to 30% by volume a third organic solvent-in-water to obtain an eluent containing the compound of formula II having a purity of 80% or higher; and iii) concentrating the eluent, and then purifying and isolating with a fourth organic solvent to obtain the compound of formula II. The above process can substantially increase the effective yield and purity of the compound of formula II.

The absorbent resin used in the above process for recovering and purifying the compound of formula II is a porous polystyrene adsorbent resin consisted of styrene, methyl acrylate, or a mixture thereof. And the third organic solvent is selected from the group consisting of methanol, ethanol, 1-propanol, isopropyl alcohol, n-butanol, acetone, tetrahydrofuran, acetonitrile, and mixtures thereof. And the fourth organic solvent is selected from the group consisting of methanol, ethanol, 1-propanol, isopropyl alcohol, n-butanol, tetrahydrofuran, methyl acetate, and mixtures thereof.

Special preference is given to the compounds Ia, Ib mentioned in the Examples, especially each individual compound, and a process for recovering and purifying the compound of formula II.

The present relates especially to the reaction steps and new intermediate compounds mentioned in the following Examples. Although the present invention has been described with reference to the preferred embodiments thereof, it is apparent to those skilled in the art that a variety of modifications and changes may be made without departing from the scope of the present invention which is intended to be defined by the appended claims.

Example 1

A) Preparation a Compound of Formula Ia

The compound of formula III (43.2 g) is slurried in DCM (777 ml). Followed by adding $Rh_2Oct_4$ (145 mg) to the solution. The mixture is heated at reflux for 7 hours then distills the resulting solution to remove 4-Dicyanomethylene-2-methyl-6-p-dimethylaminostyryl-4H-pyran (DCM, 388 mL). The compound of formula IV in dichloromethane solution is cooled to less than −35° C. The bis(2,4-dichlorophenyl)chlorophosphate (71.3 g) and the mixture of diisopropyl ethylamine (17.63 g) and 4-dimethylamino pyridine (40 mg) in DCM (43 ml) are added to the reaction solution at less than −35° C. The reaction solution is aged for 2 hours. Then extracted it by 1% $HCl_{(aq)}$ (100 mL) and 5% $NaHCO_{3(aq)}$ (100 mL) at 0~5° C. The resulting dichloromethane solution is obtained as a compound of formula Ia and taken for Example 2A, 4A and 4B.

B) Preparation a Compound of Formula Ib

The compound of formula III (43.2 g) is slurried in DCM (389 ml). Followed by adding $Rh_2Oct_4$ (130 mg) to the solution. The mixture is heated at reflux for 6 hours. The compound of formula IV in dichloromethane solution is cooled to less than −5° C. The bisphenyl chlorophosphate (32.7 g) and the mixture of diisopropyl ethylamine (18.6 g) and 4-dimethylamino pyridine (0.2 g) in DCM (43.2 ml) are added to the reaction solution at less than −5° C. The reaction solution is aged for 2 hours. Then extracted it by 1% HCl$_{(aq)}$ (200 mL) and 5% NaHCO$_{3(aq)}$ (200 mL) at 0~5° C. and crystallized from ethyl acetate and heptanes. The resulting solid is obtained as a compound of formula Ib and taken for Example 2B.

Example 2

A) Preparation of a Compound of Formula VI from Formula Ia

To provide p-nitrobenzyl(1R,5S,6S)-6-[(IR)-1-hydroxyethyl]-2-[(bis(2,4-dichlorophenyl)phosphono)oxy]-1-methylcarbapen-2-em-3-carboxylate of formula Ia in dichloromethane (500 mL) from Example 1A at −30° C., 3-([[(2S, 4S)-mercapto-2-pyrrolidinyl-1-(4-nitrobenzyloxy)carbonyl]carbonyl]amino]benzoic acid (44.7 g) was added. To the reaction mixture, diisopropylethylamine (41.0 g) was added at −30° C. and stirred. After completion of reaction water (500 mL) were added to resulting mixture into, stirred, and separated. The organic layer was obtained to yield the compound of formula VI and taken for subsequent step described in Example 3A and 3B.

B) Preparation of a Compound of Formula VI from Formula Ib

To provide p-nitrobenzyl(1R,5S,6S)-6-[(IR)-1-hydroxyethyl]-2-[(di-phenylphosphono)oxy]-1-methylcarbapen-2-em-3-carboxylate of formula Ib (119 g) obtained from Example 1B in acetonitrile (560 g) at −5° C., 3-([[(2S,4S)-mercapto-2-pyrrolidinyl-1-(4-nitrobenzyloxy)carbonyl]carbonyl]amino]benzoic acid (90 g) was added. To the reaction mixture, diisopropylethylamine (72 g) was added at −10° C. and stirred. After completion of reaction, the reaction solution was distilled to remove acetonitrile. Water (1.8 kg) and dichloromethane (1.6 kg) were added to resulting mixture into, stirred, and separated. The organic layer was obtained to yield the compound of formula VI and taken for subsequent step described in Example 3C.

C) Preparation of a Compound of Formula VI from Formula Ib

To provide p-nitrobenzyl(1R,5S,6S)-6-[(IR)-1-hydroxyethyl]-2-[(di-phenylphosphono)oxy]-1-methylcarbapen-2-em-3-carboxylate of formula Ib (119 g) purchased from SHI-LANG (Zhuoli Group)-Pharma (NANJING) CO., LTD in acetonitrile (560 g) at −5° C., 3-([[(2S,4S)-mercapto-2-pyrrolidinyl-1-(4-nitrobenzyloxy)carbonyl]carbonyl]amino]benzoic acid (90 g) was added. To the reaction mixture, diisopropylethylamine (72 g) was added at −10° C. and stirred. After completion of reaction the reaction solution was distilled to remove acetonitrile. Water (1.8 kg) and dichloromethane (1.6 kg) were added to resulting mixture into, stirred, and separated. The organic layer was obtained to yield the compound of formula VI and taken for subsequent step described in Example 3D.

Example 3

A) Preparation of a Compound of Formula II, R=H

The compound of formula VI in dichloromethane solution from Example 2A was added to the 10% Pd on carbon (48 g) with purified process water (648 mL) and sodium bicarbonate (37.2 g) at 20.0° C. Conduct hydrogen gas replacement twice for the nitrogen in the reactor. Then adjust the pressure from 25 psi to 80 psi during first one hour under hydrogen. Control reaction temperature was at 20° C. for 4~5 hours. Cool down the reaction temperature to be less than 10° C. Then adjust the pH value to about 5.0 with 5% HCl. Filter 10% Pd/C out and separate aqueous layer. The pH value of the aqueous layer was adjusted to be about 6.50 and then extract by adding dichloromethane (about 1 kg). n-Butanol (3 kg, 2 kg) is used to extract the resulting aqueous solution twice at 0~5° C. The aqueous solution is filtered through 0.22 µm filter. Isopropanol (66 ml) is added to concentrated aqueous solution (330 ml; ~100 mg/ml) at −2 to 5° C. Then cool to −8 to 0° C. and charge the mixture of methanol and tetrahydrofuran (99 ml; 2/1; V/V). Adjust the pH value by 20% acetic acid in methanol to be about 5.7 at −8° C. to −5° C. The mixture solvent of IPA, methanol and tetrahydrofuran (148.5 ml; 4/2/1; V/V) is added to resulting solution again. Seed (0.7 g, etrapenem sodium; >98% purity) is added to the mixture and aged for 2 hour. The mixture solvent of IPA, methanol and tetrahydrofuran (346.5 ml; 0.15/2/1; V/V) is added to resulting solution at −5 to −15° C. and aged for more than 5 hours. Filter the solid, wash the wet cake by mixture solvent of methanol and tetrahydrofuran (60 ml; 1/2; V/V) and press with nitrogen to filtration to remove the solvents until LOD<13%. Yield product with 26.4 g, >98% purity, LOD=8%.

B) Preparation of a Compound of Formula II, R=H

The compound of formula VI in dichloromethane solution from Example 2A was distilled to remove dichloromethane and dissolved in acetonitrile (560 g), and then was added to the 10% Pd on carbon (71 g) with purified process water (1.2 Kg) and sodium bicarbonate (67 g) at 10.0° C. Conduct hydrogen gas replacement twice for the nitrogen in the reactor. Then adjust the pressure from 80 psi to 120 psi during first one hour under hydrogen. Control reaction temperature was at 0~10° C. for 4~5 hours. Cool down the reaction temperature to be less than 5° C. Then adjust the pH value to about 5.0~5.4 with 5% HCl. Filter 10% Pd/C out and separate aqueous layer. The pH value of the aqueous layer was adjusted to be about 6.3~6.7 and then extract by adding activated carbon (about 11.9 g). After mixing, acetonitrile is removed by distillation, and then the aqueous solution was filtered out the activated carbon. The filtrate was added dichloromethane (about 1 kg). n-Butanol (7.5 kg, 4.5 kg) is used to extract the resulting aqueous solution at 0~5° C. The aqueous solution is filtered through 0.22 µm filter.

Isopropanol (100 ml) is added to concentrated aqueous solution (500 ml; ~120 mg/ml) at −2 to 5° C. Then cool to −8 to 0° C. and charge the mixture of methanol and tetrahydrofuran (150 ml; 2/1; V/V). Adjust the pH value by 20% acetic acid in methanol to be about 5.7 at −8° C. to −5° C. The mixture solvent of IPA, methanol and tetrahydrofuran (225 ml; 4/2/1; V/V) is added to resulting solution again. Seed (1 g, etrapenem sodium; >98% purity) is added to the mixture and aged for 1 hour.

The mixture solvent of IPA, methanol and tetrahydrofuran (525 ml; 0.15/2/1; V/V) is added to resulting solution at −5 to −15° C. and aged for more than 5~16 hours. Filter to obtain the solid, wash the wet cake by mixture solvent of methanol and tetrahydrofuran (80 ml; 1/2; V/V) and press with nitrogen to filtration to remove the solvents until LOD<16%. Yield product with 64.09 g, >98% purity, LOD=8%.

C) Preparation of a Compound of Formula II, R=H

The compound of formula VI in dichloromethane solution from Example 2B was added to the 10% Pd on carbon (71 g) with purified process water (1.2 kg) and sodium bicarbonate (67 g) at 20.0° C. Conduct hydrogen gas replacement twice for the nitrogen in the reactor. Then adjust the pressure from 25 psi to 80 psi during first one hour under hydrogen. Control reaction temperature was at 20° C. for 4~5 hours. Cool down the reaction temperature to be less than 10° C. Then adjust the pH value to about 5.0 with 5% HCl. Filter 10% Pd/C out and separate aqueous layer. The pH value of the aqueous layer was adjusted to be about 6.50 and then extract by adding dichloromethane (about 1 kg). n-Butanol (7.5 kg, 4.5 kg) is used to extract the resulting aqueous solution twice at 0~5° C. The aqueous solution is filtered through 0.22 μm filter.

The mixture of methanol and tetrahydrofuran (250 ml; 1/2; V/V) is added to concentrated aqueous solution (500 ml; ~100 mg/ml) at −2 to 5° C. Adjust the pH value by 20% acetic acid in methanol to be about 5.7 at −3 C to 0° C. The mixture solvent of methanol and tetrahydrofuran (250 ml; 1/2; V/V) is added to resulting solution again. Seed (1.0 g, etrapenem sodium; >98% purity) is added to the mixture at −8 to −5° C. and aged for 1 hour. The mixture solvent of methanol and tetrahydrofuran (1000 ml; 1/2; V/V) is added to resulting solution at −5 to −15° C. and aged for more than 5 hours. Filter the solid, wash the wet cake by mixture solvent of methanol and tetrahydrofuran (80 ml; 1/2; V/V) and press with nitrogen to filtration to remove the solvents until LOD<13%. Yield crude product with 56.0 g, >98% purity, LOD=7%.

The compound of formula Ia in reaction solution will be reacted with sulfur side chain directly without isolation to generate VI, VIII, or X with >90% purity (see Table 1). Followed by hydrogenation and crystallization to get the final products such as carbapenem, Meropenem, Doripenem, and Ertapenem.

TABLE 1

| Example | Intermediate | Yield (from III to II)* | Purity* |
|---|---|---|---|
| 3A | Formula Ia Heterogeneous Hydrogenation | 63.3% | 82.5% |
| 3B | Formula Ia homogeneous hydrogenation | 65.8% | 85.2% |
| 3C | Formula Ib Heterogeneous Hydrogenation | 60.2% | 79.3% |

*The yield and purity were obtained after hydrogenation.

D.1) Preparation of a Compound of Formula II, R=H

The compound of formula VI in dichloromethane solution from Example 2C was added to the 10% Pd on carbon (71 g) with purified process water (1.2 kg) and sodium bicarbonate (67 g) at 20.0° C. Conduct hydrogen gas replacement twice for the nitrogen in the reactor. Then adjust the pressure from 25 psi to 80 psi during first one hour under hydrogen. Control reaction temperature was at 20° C. for 4~5 hours. Cool down the reaction temperature to be less than 10° C. Then adjust the pH value to about 5.0 with 5% HCl. Filter 10% Pd/C out and separate aqueous layer. The pH value of the aqueous layer was adjusted to be about 6.50 and then extract by adding dichloromethane (about 1 kg). n-Butanol (7.5 kg, 4.5 kg) is used to extract the resulting aqueous solution twice at 0~5° C. The aqueous solution is filtered through 0.22 μm filter.

Isopropanol (100 ml) is added to the concentrated aqueous solution (500 ml; ~100 mg/ml) at −2 to 5° C. Then cool to −8 to 0° C. and charge the mixture of methanol and methyl acetate (150 ml; 2/1; V/V). Adjust the pH value by 20% acetic acid in methanol to be about 5.7 at −8° C. to −5° C. The mixture solvent of IPA, methanol and methyl acetate (225 ml; 4/2/1; V/V) is added to resulting solution again. Seed (1.0 g, etrapenem sodium; >98% purity) is added to the mixture and aged for 1 hour. The mixture solvent of IPA, methanol and methyl acetate (525 ml; 0.15/2/1; V/V) is added to resulting solution at −5 to −15° C. and aged for more than 5 hours. Filter the solid, wash the wet cake by mixture solvent of methanol and methyl acetate (80 ml; 1/2; V/V) and press with nitrogen to filtration to remove the solvents until LOD<13%. Yield crude product with 54.8 g, >98% purity, LOD=11%.

D.2) Preparation of a Compound of Formula II, R=H

The compound of formula VI in dichloromethane solution from Example 2C was added to the 10% Pd on carbon (71 g) with purified process water (1.2 kg) and sodium bicarbonate (67 g) at 20.0° C. Conduct hydrogen gas replacement twice for the nitrogen in the reactor. Then adjust the pressure from 25 psi to 80 psi during first one hour under hydrogen. Control reaction temperature was at 20° C. for 4~5 hours. Cool down the reaction temperature to be less than 10° C. Then adjust pH value to about 5.0 with 5% HCl. Filter 10% Pd/C out and separate aqueous layer. The pH value of the aqueous layer was adjusted to be about 6.50 and then extract by adding dichloromethane (about 1 kg). n-Butanol (7.5 kg, 4.5 kg) is used to extract the resulting aqueous solution twice at 0~5° C. The aqueous solution is filtered through 0.22 μm filter. Isopropanol (100 ml) is added to the concentrated aqueous solution (500 ml; ~100 mg/ml) at −2 to 5° C. Then cool to −8 to 0° C. and charge the mixture of methanol and tetrahydrofuran (150 ml; 2/1; V/V). Adjust the pH value by 20% acetic acid in methanol to be about 5.7 at −8° C. to −5° C. The mixture solvent of IPA, methanol and tetrahydrofuran (225 ml; 4/2/1; V/V) is added to resulting solution again. Seed (1.0 g, etrapenem sodium; >98% purity) is added to the mixture and aged for 1 hour.

The mixture solvent of 1-propanol, methanol and tetrahydrofuran (525 ml; 0.15/2/1; V/V) is added to resulting solution at −5 to −15° C. and aged for more than 5 hours. Filter the solid, wash the wet cake by mixture solvent of 1-propanol, methanol and tetrahydrofuran (80 ml; 1/1/2; V/V) and press with nitrogen to filtration to remove the solvents until LOD<13%. Yield product with 56.1 g, >98% purity, LOD=10%.

D.3) Preparation of a Compound of Formula II, R=H

The compound of formula VI in dichloromethane solution from Example 2C was added to the 10% Pd on carbon (71 g) with purified process water (1.2 kg) and sodium bicarbonate (67 g) at 20.0° C. Conduct hydrogen gas replacement twice for the nitrogen in the reactor. Then adjust the pressure from 25 psi to 80 psi during first one hour under hydrogen. Control reaction temperature was at 20° C. for 4~5 hours. Cool down the reaction temperature to be less than 10° C. Then adjust pH value to about 5.0 with 5% HCl. Filter 10% Pd/C out and separate organic layer. The pH value of the aqueous layer was adjusted to be about 6.50 and then extract by adding dichloromethane (about 1 kg).

Iso-amyl alcohol (12 kg, 8 kg) is used to extract the resulting aqueous solution twice at 0-5° C. The aqueous solution is filtered through 0.22 μm filter. Isopropanol (100 ml) is added to concentrated aqueous solution (500 ml; ~100 mg/ml) at −2 to 5° C. Then cool to −8 to 0° C. and charge the mixture of methanol and tetrahydrofuran (150 ml; 2/1; V/V). Adjust the pH value by 20% acetic acid in methanol to be about 5.7 at −8° C. to −5° C. The mixture solvent of IPA, methanol and tetrahydrofuran (225 ml; 4/2/1; V/V) is added to resulting solution again. Seed (1.0 g, etrapenem sodium; >98% purity) is added to the mixture and aged for 1 hour. The mixture solvent of IPA, methanol and tetrahydrofuran (525 ml; 0.15/2/1; V/V) is added to resulting solution at −5 to −15° C. and aged for more than 5 hours. Filter the solid, wash the wet cake by mixture solvent of methanol and tetrahydrofuran (80 ml;

1/2; V/V) and press with nitrogen to filtration to remove the solvents until LOD<13%. Yield product with 55.8 g, >98% purity, LOD=10%.

D.4) Preparation of a Compound of Formula II, R=H

The compound of formula VI in dichloromethane solution from Example 2C was distilled to remove dichloromethane and dissolved in acetonitrile (560 g), and then was added to the 10% Pd on carbon (71 g) with purified process water (1.2 Kg) and sodium bicarbonate (67 g) at 10.0° C. Conduct hydrogen gas replacement twice for the nitrogen in the reactor. Then adjust the pressure from 80 psi to 120 psi during first one hour under hydrogen. Control reaction temperature was at 0~10° C. for 4~5 hours. Cool down the reaction temperature to be less than 5° C. Then adjust the pH value to about 5.0~5.4 with 5% HCl. Filter 10% Pd/C out and separate aqueous layer. The pH value of the aqueous layer was adjusted to be about 6.3~6.7 and then extract by adding activated carbon (about 11.9 g). After mixing, acetonitrile is removed by distillation, and then the aqueous solution was filtered out the activated carbon. The filtrate was added dichloromethane (about 1 kg). n-Butanol (7.5 kg, 4.5 kg) is used to extract the resulting aqueous solution at 0~5° C. The aqueous solution is filtered through 0.22 µm filter.

Isopropanol (100 ml) is added to concentrated aqueous solution (500 ml; ~120 mg/ml) at −2 to 5° C. Then cool to −8 to 0° C. and charge the mixture of methanol and tetrahydrofuran (150 ml; 2/1; V/V). Adjust the pH value by 20% acetic acid in methanol to be about 5.7 at −8° C. to −5° C. The mixture solvent of IPA, methanol and tetrahydrofuran (225 ml; 4/2/1; V/V) is added to resulting solution again. Seed (1 g, etrapenem sodium; >98% purity) is added to the mixture and aged for 1 hour.

The mixture solvent of IPA, methanol and tetrahydrofuran (525 ml; 0.15/2/1; V/V) is added to resulting solution at −5 to −15° C. and aged for more than 5~16 hours. Filter to obtain the solid, wash the wet cake by mixture solvent of methanol and tetrahydrofuran (80 ml; 1/2; V/V) and press with nitrogen to filtration to remove the solvents until LOD<16%. Yield product with 55.8 g, >98% purity, LOD=8%.

D.5) Preparation of a Compound of Formula II, R=H

The compound of formula VI in dichloromethane solution from Example 2C was distilled to remove dichloromethane and dissolved in acetonitrile (560 g), and then was added to the 10% Pd on carbon (71 g) with purified process water (1.2 Kg) and sodium bicarbonate (67 g) at 10.0° C. Conduct hydrogen gas replacement twice for the nitrogen in the reactor. Then adjust the pressure from 80 psi to 120 psi during first one hour under hydrogen. Control reaction temperature was at 0~10° C. for 4~5 hours. Cool down the reaction temperature to be less than 5° C. Then adjust the pH value to about 5.0~5.4 with 5% HCl. Filter 10% Pd/C out and separate aqueous layer. The pH value of the aqueous layer was adjusted to be about 6.5 and then extract by adding activated carbon (about 11.9 g). After mixing, acetonitrile is removed by distillation, and then the aqueous solution was filtered out the activated carbon. The filtrate was added dichloromethane (about 1 kg). n-Butanol (7.5 kg, 4.5 kg) is used to extract the resulting aqueous solution at 0~5° C. The aqueous solution is filtered through 0.22 µm filter.

A mixture of methanol and tetrahydrofuran (250 ml; 1/2; V/V) is added to concentrated aqueous solution (500 ml; ~100 mg/ml) at −2 to 2° C. Then cool to −3 to 0° C. and charge the mixture of methanol and tetrahydrofuran (250 ml; 1/2; V/V). Seed (1 g, etrapenem sodium; >98% purity) is added to the mixture and aged for 1 hour at −8° C. to −5° C. The mixture solvent of methanol and tetrahydrofuran (1000 ml; 1/2; V/V) is added to resulting solution again at −8° C. to −15° C. and aged for more than 5 hours. Filter to obtain the solid, wash the wet cake by mixture solvent of methanol and tetrahydrofuran (100 ml; 1/2; V/V) and press with nitrogen to filtration to remove the solvents until LOD<16%. Yield product with 57.1 g, >98% purity, LOD=7%.

Example 4

A) Preparation of a Compound of Formula VIII

To provide p-nitrobenzyl(1R,5S,6S)-6-[(1R)-1-hydroxyethyl]-2-[(bis(2,4-dichlorophenyl)phosphono)oxy]-1-methylcarbapen-2-em-3-carboxylate of formula Ia in dichloromethane (500 mL) from Example 1A at −35° C., (2S,4S)-2-(dimethyl-aminocarbonyl)-4-mercapto-1-(p-nitrobenzyloxycarbonyl)-1-pyrrolidine (33.6 g) was added. To the reaction mixture, diisopropylethylamine (32.3 g) was added at −30° C. and stirred. After completion of reaction, the resulting mixture was washed with 5% $NaHCO_3$ aqueous (500 ml) and water (500 ml) and separated. The organic layer was obtained to yield the compound of formula VIII and taken for subsequent step described in Example 5A.

B) Preparation of a Compound of Formula X

To provide p-nitrobenzyl(1R,5S,6S)-6-[(1R)-1-hydroxyethyl]-2-[(bis(2,4-dichlorophenyl)phosphono)oxy]-1-methylcarbapen-2-em-3-carboxylate of formula Ia in dichloromethane (500 mL) from Example 1A at −35° C., (2S,4S)-1-p-nitrobenzyloxycarbonyl-2-sulfamoylaminomethyl-4-mercaptopyrrolidine (39.0 g) was added. To the reaction mixture, diisopropylethylamine (32.3 g) was added at −30° C. and stirred. After completion of reaction, the resulting mixture was washed with 5% $NaHCO_3$ aqueous (500 ml) and water (500 ml) and separated. The organic layer was obtained to yield the compound of formula X and taken for subsequent step described in Example 5B.

Example 5

A) Preparation of Meropenem

The compound of formula VIII in dichloromethane solution from Example 4A was distilled to remove dichloromethane. Add tetrahydrofuran (1000 mL) into the condensed solution and stir until the complete dissolution. Deionized water (800 mL), 10% wt % Pd/C (8.0 g), and 2,6-dimethylpyridine (22 g) were added to the solution. The suspension was stirred at 20~25° C. for 1 to 2 h under a $H_2$ atmosphere (1.8 MPa). The used Pd/C was removed by filtration and washed with a mixture of tetrahydrofuran (72 mL) and deionized water (48 mL). The filtrate was diluted with acetone (3200 mL) and seed crystals were added at 5 to 10° C. After 0.5 h, substantive crystals were precipitated. Acetone (1600 mL) was added slowly at 5 to 10° C. After the mixture was stirred for 1 h, the crystals were collected by filtration, washed with acetone (150 mL) and dried to give Meropenem 20.8 g.

B) Preparation of Doripenem

The compound of formula X in dichloromethane solution from Example 4B was distilled to remove dichloromethane and dissolved in tetrahydrofuran (470 ml). Deionized water (310 mL), 10% wt % Pd/C (39.8 g), and $MgCl_2.6H_2O$ (11.1 g) were added to the solution. The suspension was stirred from 25 to 35° C. for 2 to 3 h under a $H_2$ atmosphere (0.5 MPa). The used Pd/C was removed by filtration and washed with a mixture of tetrahydrofuran (140 mL) and deionized water (95 mL). $MgCl_2.6H_2O$ (5.5 g) was dissolved in the combined filtrates. After addition of tetrahydrofuran (2300 mL) to the mixture, the aqueous layer was separated at 23~28° C. After cooling the extract to 0~5° C., MeOH (310 mL) and seed crystals (0.1 g) were added to the extract. After MgCl$_2$.6H$_2$O (5.5 g×2) was added to the organic layer, the resulting aqueous layer was separated and added to the previous aqueous suspension. MeOH (590 mL) was added dropwise to the suspension. The mixture was stirred at −10~−15° C. for 2 h. The solid was collected by filtration, washed with MeOH, and dried to give Doripenem 29.5 g.

Example 6

A) Recovery of a Compound of Formula II from Resulting Solution, R═H

The resulting solution containing the compound of formula II (1000 ml; ~4.8 mg/ml) from Example 3 D.3 was extracted by adding dichloromethane (1000 ml) at 0~5° C. Then extracted and separated the reaction solution by ethyl acetate (500 ml, 250 ml). The resulting aqueous layer was concentrated for 1 hour at less than 20° C. to obtain a solution containing the compound of formula II (200 ml; ~26.91 mg/ml), which yield the compound of formula II (~5.38 g).

The solution (26.91 mg/ml; 50.8% purity) obtained from above step was slowly passed through the high porous polystyrene adsorption resin HP-20 of the 253 mm×25 mm tube column at 0~5° C. for about 30 minutes. The resin is consisted of styrene, methyl acrylate, or a mixture thereof. The column was washed with 4 column volumes of purified process water at a flow rate of 1 ml/min, and then increase flow rate to 2 ml/min with 10 column volumes. The 10% methanol solution was then washed into the column with 10 column volumes. Fraction 4 to fraction 18 were collected (1 column volume) and product fractions 4-18 contained 71.5% of the compound of formula II. The volume of the product fractions is condensed by the extraction of n-butanol, and the product fractions was adequate for further purification via crystallization according to Example 3 D.2) to obtain high concentration of formula II product. The purity and percent recovery of formula II product was with 96.5% and 52.0% respectively (by HPLC).

B) Recovery of a Compound of Formula II from Resulting Solution, R═H

The resulting solution containing the compound of formula II (1300 ml; ~5 mg/ml) from Example 3 D.3) was extracted by adding dichloromethane (975 ml) at 0~5° C. Then extracted and separated the reaction solution by ethyl acetate (560 ml, 300 ml). The resulting aqueous layer was concentrated for 1 hour at less than 10° C. to obtain a solution containing the compound of formula II (220 ml; ~29.65 mg/ml), which yield the compound of formula II (~5.93 g).

The solution (29.65 mg/ml; 48% purity) obtained from above step was slowly passed through the high porous polystyrene adsorption resin SX-10 of the 253 mm×25 mm tube column at 0~5° C. for about 30 minutes. The column was washed with 4 column volumes of purified process water at a flow rate of 1 ml/min, and then increase flow rate to 2 ml/min with 25 column volumes. Fraction 4 to fraction 22 were collected (1 column volume) and product fractions 4-22 contained 73.1% of the compound of formula II. The volume of the product fractions is condensed by the extraction of n-butanol, and the product fractions was adequate for further purification via crystallization according to Example 3 D.2) to obtain high concentration of formula II product. The purity and percent recovery of formula II product was with 96.8% and 53.7% respectively (by HPLC).

A number of embodiments of the invention have been described. Nevertheless, it will be understood that various modifications may be made without departing from the spirit and scope of the invention. Accordingly, other embodiments are within the scope of the following claims.

What is claimed is:

1. A process for the preparation of a compound of formula II:

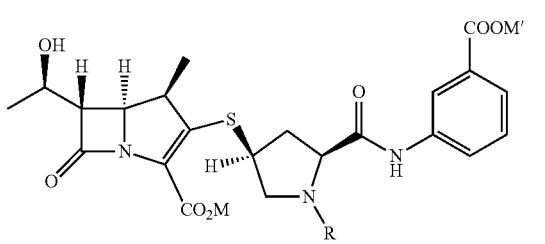

or a pharmaceutically acceptable salt thereof, wherein R is hydrogen and M and M' are hydrogen, sodium ion, or potassium ion comprising:

i) providing a compound of formula I:

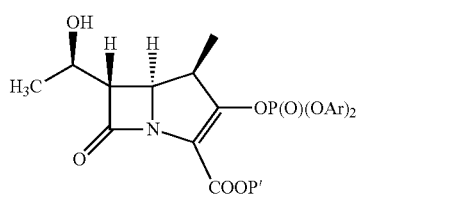

ii) converting the compound of formula I into the compound of formula II, wherein Ar is 2,4-dichlorophenyl or phenyl, P is phosphorous, and P' is selected from the group consisting of alkyl, 2,2,2,-trichloroethyl, 2-bromoethyl, benzhydryl, trityl, aryl, trimethylsilyl, triethylsilyl, 4-methoxybenzyl, t-butyl, p-nitrobenzyl and hydrogen; and wherein the converting comprises the step of condensing the compound of formula I with a compound of formula V:

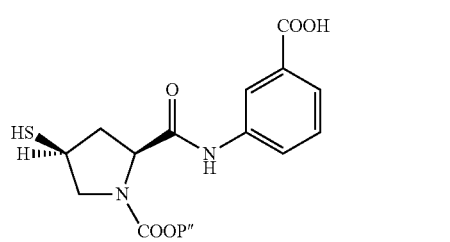

to form a compound of formula VI:

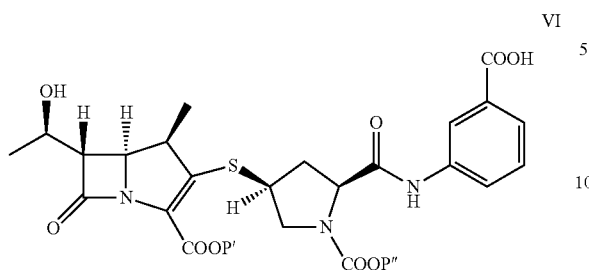

wherein P'' is selected from the group consisting of alkyl, 2,2,2,-trichloroethyl, dibromoethyl, benzhydryl, trityl, aryl, trimethylsilyl, triethylsilyl, 4-methoxybenzyl, t-butyl, p-nitrobenzyl and hydrogen;

wherein the compound of formula VI is converted into the compound of formula II by hydrogenolysis in presence of a metal catalyst, a base, water and a first organic solvent to produce a first solution of the compound of formula II, and the compound of formula II is obtained from the first solution of the compound of formula II by (a) adjusting a pH value to 5.0 to 5.4 of the first solution of the compound of formula II and then filtering out the metal catalyst;

(b) separating an aqueous layer from the first solution of the compound of formula II and removing the first organic solvent from the aqueous layer by distillation or extraction;

(c) extracting a first aqueous concentrated extract from the aqueous layer with dichloromethane under the pH value of the aqueous layer adjusted to 6.3-6.7, and then extracting a second aqueous concentrated extract with n-butanol or isoamyl alcohol (IAA);

(d) filtering the second aqueous concentrated extract to obtain an aqueous concentrated solution and adding isopropanol (IPA) or a mixture of methanol and tetrahydrofuran in the aqueous concentrated solution then chilled to a temperature of −8~0° C.;

(e) adding a mixture of methanol and tetrahydrofuran or a mixture of methanol and methyl acetate in the aqueous concentrated solution and adjusting the pH value to 5.7 thereof;

(f) adding a mixture solvent of isopropanol, methanol and tetrahydrofuran or a mixture solvent of methanol and tetrahydrofuran, or a mixture of IPA, methanol and methyl acetate in the aqueous concentrated solution and adding a seed material to the aqueous concentrated solution to age thereof;

(g) adding a crystallization solvent into the aqueous concentrated solution to crystallization then the aqueous concentrated solution is chilled to a temperature of −5~−15° C. and filtering to obtain a crystalline compound of formula II and residual liquid; and (h) washing the crystalline compound of formula II with a mixture of methanol and tetrahydrofuran or a mixture of 1-propanol, methanol and tetrahydrofuran, or a mixture of methanol and methyl acetate, and pressing with nitrogen to remove the crystallization solvent to yield the compound of formula II, the first organic solvent is selected from the group consisting of tetrahydrofuran, acetonitrile, ethylacetate, propionitrile, n-butanol, methanol, ethanol, dichloromethane, NN-dimethylformamide, N-ethylpyrrolidinone, and mixtures thereof; and the crystallization solvent is a mixture selected from the group consisting of:
(i) IPA, methanol and tetrahydrofuran;
(ii) methanol and tetrahydrofuran;
(iii) IPA, methanol and methyl acetate; and
(iv) 1-propanol, methanol and tetrahydrofuran.

2. The process according to claim 1, wherein the compound of formula I is converted into the compound of formula VI by using a solvent selected from the group consisting of diethyl ether, tetrahydrofuran, toluene, xylene, dichloromethane, 1,2-dichloroethane, NN-dimethylformamide, dimethylacetamide, N-methylpyrrolidinone, N-ethylpyrrolidinone, N-methylpiperidinone, acetonitrile, propionitrile, and mixtures thereof.

3. The process according to claim 1, wherein the metal catalyst is palladium, platinum, rhodium, and mixtures thereof.

4. The process according to claim 1, wherein the base is bicarbonate and used for adjusting the first solution of the compound of formula II with pH of 6 to 9.

5. The process according to claim 1, wherein the step (c) of extracting with an alcohol is conducted using a multi-stage countercurrent centrifugal extractor.

6. The process according to claim 1, wherein the compound of formula I is prepared by a process comprising:
   i) cyclizing a compound of formula III:

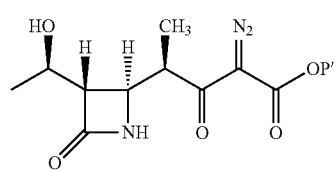

with $Rh_2(Oct_4)$ in dichloromethane to obtain a compound of formula IV, wherein Oct is octanoate:

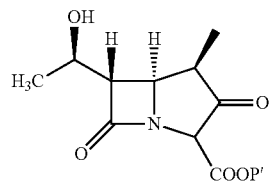

ii) reacting the compound of formula IV with bis(2,4-dichlorophenyl)-chlorophosphate in the presence of a base to obtain the compound of formula I.

7. The process according to claim 6, wherein the step (i) is performed using a solvent selected from the group consisting of dichloromethane, methyl acetate, ethyl acetate, toluene, tetrahydrofuran, acetonitrile, and mixtures thereof.

8. The process according to claim 6, wherein step (ii) is performed using a base selected from the group consisting of diisopropylethylamine (DIPEA), diisopropylamine (DIPA), dicyclohexylamine (DCHA), 2,2,6,6-tetra-methylpiperidine (TMP), 1,1,3,3-tetramethylguanidine (TMG), 1,8-diazabicyclo[4.3.0.]undec-7-ene(DBU)1,5-diazabicyclo[4.3.0]non-5-ene (DBN), N-methylpyrrolidine, N,N-dimethylaminopyridine, N,N-diethylamino pyridine potassium hydroxide, sodium carbonate, sodium hydrogen carbonate, and disodium hydrogen phosphate.

9. The process according to claim 6, wherein P' is p-nitrobenzyl.

10. A process for the preparation of a compound of Meropenem:

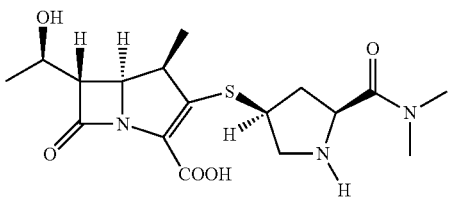 [SMILES: C[C@@H](O)[C@H]1C(=O)N2C(C(=O)O)=C(S[C@@H]3CN[C@H](C(=O)N(C)C)C3)[C@H](C)[C@H]12]

comprising:
i) providing a compound of formula I:

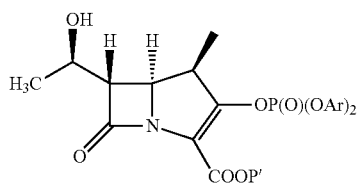

I ii) converting the compound of formula I into Meropenem, wherein Ar is 2,4-dichlorophenyl, P is phosphorous, and P' is selected from the group consisting of alkyl, 2,2,2,-trichloroethyl, 2-bromoethyl, benzhydryl, trityl, aryl, trimethylsilyl, triethylsilyl, 4-methoxybenzyl, t-butyl, p-nitrobenzyl and hydrogen; and wherein the converting comprises the step of condensing the compound of formula I with a compound of formula VII:

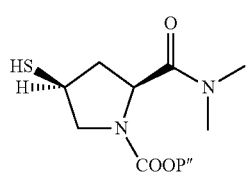

VII to form a compound of formula VIII:

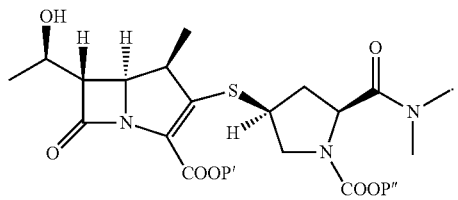

VIII wherein P" is selected from the group consisting of alkyl, 2,2,2,-trichloroethyl, 2-bromoethyl, benzhydryl, trityl, aryl, trimethylsilyl, triethylsilyl, 4-methoxybenzyl, t-butyl, p-nitrobenzyl and hydrogen;
wherein the compound of formula VIII is converted into the Meropenem by hydrogenolysis in presence of a metal catalyst, a base, water and tetrahydrofuran, and then Meropenem is obtained by (a) filtering out the metal catalyst and washing with a mixture of tetrahydrofuran and water;
(b) diluting the filtrate with acetone and adding a seed material to precipitate; and
(c) adding the acetone and filtering to collect the crystalline Meropenem.

11. A process for the preparation of a compound of Doripenem:

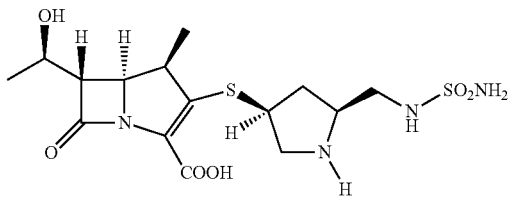 [SMILES: C[C@@H](O)[C@H]1C(=O)N2C(C(=O)O)=C(S[C@@H]3CN[C@H](CNS(N)(=O)=O)C3)[C@H](C)[C@H]12]

comprising:
i) providing a compound of formula I:

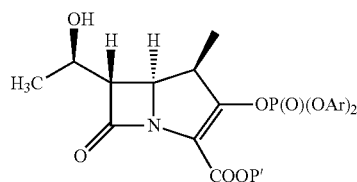

I ii) converting the compound of formula I into Doripenem, wherein Ar is 2,4-dichlorophenyl, P is phosphorous, and P' is selected from the group consisting of alkyl, 2,2,2,-trichloroethyl, 2-bromoethyl, benzhydryl, trityl, aryl, trimethylsilyl, triethylsilyl, 4-methoxybenzyl, t-butyl, p-nitrobenzyl and hydrogen; and wherein the converting comprises the step of condensing the compound of formula I with a compound of formula IX:

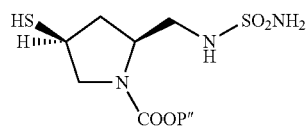

IX to form a compound of formula X:

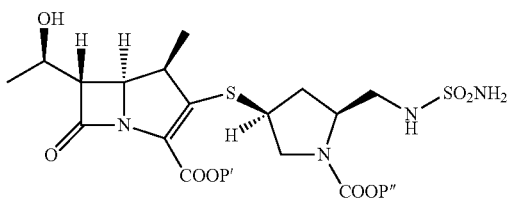

X wherein P" is selected from the group consisting of alkyl, 2,2,2,-trichloroethyl, 2-bromoethyl, benzhydryl, trityl, aryl, trimethylsilyl, triethylsilyl, 4-methoxybenzyl, t-butyl, p-nitrobenzyl and hydrogen;

wherein the compound of formula X is converted into the Doripenem by hydrogenolysis in presence of a suspension of a metal catalyst, a base, water, tetrahydrofuran and MgCl$_2$.6H$_2$O, and then Doripenem is obtained by
- (a) filtering out the metal catalyst from the suspension and washing with a mixture of tetrahydrofuran and water;
- (b) adding MgCl$_2$.6H$_2$O and tetrahydrofuran in a filtrate and forming a first aqueous layer and an organic layer of the filtrate then cooling the first aqueous layer of the filtrate to 0~5° C.:
- (c) adding a seed material and methanol in the first aqueous layer of the filtrate to form a aqueous suspension;
- (d) adding MgCl$_2$.6H$_2$O to the organic layer of the filtrate to form a second aqueous layer then mixing the second aqueous layer with the aqueous suspension of step (c); and
- (e) adding methanol into the aqueous suspension of step (d) and filtering to collect the crystalline Doripenem.

12. A process for recovering and purifying additional compound of formula II from the residual liquid according to claim 1; comprising:
- i) removing the crystallization solvent from the residual liquid according to claim 1 with a extracting solvent, and then separating the extracting solvent to yield an aqueous second solution containing the compound of formula II, wherein the extracting solvent is dichloromethane, ethyl acetate, toluene, or xylene;
- ii) passing the second solution through an absorbent adsorbent resin for removing impurities and desorbing the compound of formula II from the adsorbent resin by eluting with a mixture of 0% to 10% by volume a third organic solvent and the rest of the mixture is water to obtain an eluent containing the compound of formula II having a purity of 80% or higher; and
- iii) concentrating the eluent with a fourth organic solvent, and subjecting the concentrated eluent to crystallization to yield additional compound of formula II;

wherein the fourth organic solvent is selected from the group consisting of methanol, ethanol, 1-propanol, isopropyl alcohol, n-butanol, tetrahydrofuran, methyl acetate, and mixtures thereof.

13. The process according to claim 12, wherein the adsorbent resin is a porous polystyrene adsorbent resin.

14. The process according to claim 12, wherein the third organic solvent is selected from the group consisting of methanol, ethanol, 1-propanol, isopropyl alcohol, n-butanol, acetone, tetrahydrofuran, acetonitrile, and mixtures thereof.

* * * * *